United States Patent [19]

Basset et al.

[11] Patent Number: 5,720,947
[45] Date of Patent: Feb. 24, 1998

[54] COMPOSITIONS FOR DEODORIZING ANIMAL EXCRETA AND DEODORIZING METHOD THEREFOR

[75] Inventors: Jacques Basset, Saint-Aubin-les-Elbeuf; Henri-Jean Caupin, Versailles; Francis Wable, Reuil-Malmaison, all of France

[73] Assignee: Elf Atochem S. A., Puteaux, France

[21] Appl. No.: 571,996

[22] PCT Filed: Jun. 22, 1994

[86] PCT No.: PCT/FR94/00755

§ 371 Date: May 15, 1996

§ 102(e) Date: May 15, 1996

[87] PCT Pub. No.: WO95/00182

PCT Pub. Date: Jan. 5, 1995

[30] Foreign Application Priority Data

Jun. 23, 1993 [FR] France .................. 93 07631

[51] Int. Cl.$^6$ .................. A61L 11/00; A61K 9/00
[52] U.S. Cl. .................. 424/76.1; 424/76.6; 424/400
[58] Field of Search .................. 424/76.1, 76.6, 424/400

[56] References Cited

U.S. PATENT DOCUMENTS

| 3,124,459 | 3/1964 | Erwin | 99/1 |
| 3,124,460 | 3/1964 | Erwin | 99/1 |
| 4,464,193 | 8/1984 | Kaneko et al. | 71/83 |
| 4,617,047 | 10/1986 | Bretzloff | 71/5 |
| 5,275,783 | 1/1994 | Menassa et al. | 422/5 |

*Primary Examiner*—Thurman K. Page
*Assistant Examiner*—Kathryne E. Shelborne
*Attorney, Agent, or Firm*—Pennie & Edmonds

[57] ABSTRACT

This composition for deodorizing animal faeces such as liquid manure, in particular liquid pig manure, is characterized in that it comprises: (a) at least one normal superphosphate; (b) at least one compound chosen from undecylenic acid, its esters and its polyoxyalkyle-mated esters; and optionally (c) sodium perborate. The constituent (a) is in particular a normal superphosphate containing approximately 16–18% by weight of $P_2O_5$. The constituent (b) is in particular methyl undecylenate.

The composition is formulated, for example, order to be able to treat animal faeces with up to approximately 10,000 ppm of the constituent (a); up to approximately 1000 ppm of the constituent (b); and up to approximately 500 ppm of active $O_2$ form the constituent (c), these amounts being calculated with respect to the weight of the animal faeces to be treated.

15 Claims, No Drawings

COMPOSITIONS FOR DEODORIZING ANIMAL EXCRETA AND DEODORIZING METHOD THEREFOR

The present invention relates to compositions for deodorizing foul-smelling animal faeces, such as liquid manure, in particular liquid pig manure, and faeces arising from poultry-rearing: ducks, chickens, and the like. The present invention also relates to the corresponding deodorizing process.

Intensive rearing is a considerable source of nuisance, the pig-rearing sector, with the liquid manure, being a not insignificant component of this. The pig population generates large amounts of liquid manure which, apart from the pollution problem caused in particular by overspreading, are sources of nuisance on account of the smells, both as regards livestock houses, with storage under slatted floors, and as regards their storage, their treatment and their spreading.

Several deodorizing systems are known. The objective of these systems is to reduce the smell and also the polluting components. These systems, which are often very expensive, since they require investments very often regarded as not productive, do not specifically, and not always efficiently, sort out the problem of the smells.

Many substances have been proposed for solving the problems of smells from animal faeces; they most often act by masking the smell, that is to say by substitution of the smells of the faeces by those which they give off.

However, the use is known, from European Patent Application EP-A-0 434 523, of undecylenic acid esters, polyoxyalkylenated with 2–10 polyoxyalkylene units, the advantage of these esters being that their own smell is not really noticeable, unlike the case with methyl undecylenate. Nevertheless, it is apparent that these deodorizing agents for liquid manure had to be further improved. It is this objective which was achieved in the present invention.

It has in fact been discovered that a composition, comprising at least two constituents from (a) normal superphosphates, (b) undecylenic acid and its esters, including methyl undecylenate, and (c) sodium perborate, always displayed, on examination of the effect/dose diagrams (as percentage of smell intensity), a potentiating effect, especially of the effect of normal superphosphate with undecylenic acid or ester and sodium perborate respectively and of sodium perborate with undecylenic acid or ester.

Another unexpected effect is that it was possible to achieve excellent results, for example at 15% of smell intensity in the case of a composition formulated in order to be able to treat faeces with 5000 ppm of normal superphosphate and 320 ppm of methyl undecylenate.

Yet another unexpected effect is observed in the fact that methyl undecylenate no longer has its own highly noticeable smell when it is, at the time of use, incorporated in the faeces in combination with the normal superphosphate or with the normal superphosphate+sodium perborate, mixing of the constituents being carried out only at the time of use, or the methyl undecylenate alternatively being incorporated separately from the other constituents in the mass to be treated. In the classification of the formulations by quality (see Table 3 below), comparison of formulations 7b, 4b and 2b, which make it possible to treat the faeces with 100 ppm of methyl undecylenate, does not result in the same percentage, as might have been expected. In fact, it is clearly shown in the European Patent Application mentioned as reference that methyl undecylenate has its own highly noticeable smell.

Moreover the compositions containing the three constituents provide excellent results, making it possible in particular to achieve values of the order of 10% of the initial smell intensity, such as, for example, with a composition formulated in order to be able to treat the faeces with 7500 ppm of normal superphosphate, 150 ppm of methyl undecylenate and 300 ppm of active $O_2$ from sodium perborate.

The first subject of the present invention is therefore compositions for deodorizing animal faeces such as liquid manure, in particular liquid pig manure, characterized in that they comprise at least two constituents from:

(a) at least one normal superphosphate;

(b) at least one compound chosen from undecylenic acid, its esters and its polyoxyalkylenated esters.

Normal superphosphates are compounds which are well known as fertilizers; they consist essentially of mixtures of the three calciumphosphates with phosphoric acid and calcium sulphate. Various varieties of them are distinguished, namely inorganic superphosphates, obtained from inorganic phosphates; bone superphosphates, obtained from defatted and crushed bones; ammonia superphosphates, which are mixtures of ammonium sulphate and calcium superphosphate; ammonia-nitrate superphosphates, which are mixtures of sodium nitrate, ammonium sulphate and superphosphate; ammonia-potassium superphosphates, which are mixtures of ammonium sulphate, superphosphate and potassium salts; and ammonia-magnesium superphosphates, which are obtained by reacting magnesium phosphate and ammonia solution.

Mention may be made, as an example of a superphosphate which can be used, of a normal superphosphate containing approximately 16–18% by weight of $P_2O_5$.

Mention may be made, among undecylenic acid esters which come under the definition of the constituent (b) of the composition in accordance with the present invention, of alkyl undecylenates, such as methyl undecylenate, and polyoxyalkylenated esters, for example containing 2 to 12 oxyalkylene units, such as polyoxyethylenated, polyoxypropylenated or poloxyethylenated-poloxypropylenated esters.

The compositions according to the invention can also, in addition to the constituents (a) and (b), comprise sodium perborate (constituent (c)).

These compositions are advantageously formulated in order to be able to treat animal faeces with:

up to 10,000 ppm of the constituent (a);

up to approximately 1000 ppm of the constituent (b); and if appropriate, up to approximately 500 ppm of active $O_2$ from the constituent (c), these mounts being calculated with respect to the weight of the animal faeces to be treated.

Such compositions are preferably formulated in order to be able to treat animal faeces with:

approximately 1000 to 5000 ppm of the constituent (a);

approximately 50 to 100 ppm of the constituent (b); and if appropriate, up to approximately 300 ppm of active $O_2$ from the constituent (c), these amounts being calculated with respect to the weight of the animal faeces to be treated.

The constituent (c) is then preferably present in an amount which makes it possible to treat the animal faeces with approximately 150 to 300 ppm of active $O_2$.

It is also possible to envisage that a deodorizing composition according to the invention additionally comprises at least one additive chosen from fungicides and bacteriostatic agents, which additives are well known to those skilled in the art.

The constituents of a deodorizing composition according to the invention can be packaged separately before use.

Moreover, each of the constituents can be provided in a pulverulent form, or else in suspension or in solution in water, or else at least partially in the form adsorbed on a porous and inert carrier such as silica or clay particles.

Another subject of the present invention is a process for deodorizing animal faeces, in particular liquid pig manure, characterized in that a deodorizing composition as defined above is incorporated, by mixing, in the animal faeces to be treated, with a view to storing or spreading them.

The mixture of the constituents can be prepared only at the time of use or else at least one constituent of the composition can be incorporated, separately from the other constituents, in the animal faeces to be treated.

In order to illustrate better the subject of the present invention, a number of implementational examples thereof will now be described below, by way of indication and without implied limitation.

FORMULATION OF EXAMPLES 1to 7

Formulations 1 to 7 of the invention, as defined in Table 1, were envisaged which make it possible to treat liquid manure with A ppm of normal superphosphate, B ppm of methyl undecylenate and C ppm of active $O_2$ from sodium perborate. The normal superphosphate used was that marketed by the Company Soferti under the trade name Biosuper.

TABLE 1

| Formulation Example | A | B | C |
|---|---|---|---|
| 1 | 1000 | 50 | 300 |
| 2 | 1000 | 100 | 0 |
| 3 | 2000 | 50 | 300 |
| 4 | 2000 | 100 | 0 |
| 5 | 2000 | 50 | 150 |
| 6 | 3000 | 50 | 150 |
| 7 | 5000 | 100 | 300 |

Each of these formulations was used as follows:

A mixture of normal superphosphate and methyl undecylenate was diluted in approximately its weight of water in an open-topped drum with a capacity of 200 l. If appropriate, sodium perborate was diluted in another drum and under the same conditions. A liquid manure tank, with a capacity of 15,000 l and equipped with a system for mixing by air homogenization, was filled to half the volume of the tank by pumping, liquid manure and the normal superphosphate and methyl undecylenate diluate being simultaneously sucked in. The sodium perborate diluate, if necessary, and the remainder of the liquid manure were then sucked into the liquid manure tank.

Moreover, two series of tests were carried out, one (series a) with a normal superphosphate and undecylenate mixture formed before use and the other (series b) with such a mixture prepared just before use.

The evaluation of each of these formulations 1a to 7a and 1b to 7b on the smell of the liquid pig manure for spreading was carried out with respect to untreated liquid manure as control. To this end, the control liquid manure and the various deodorized liquid manures in accordance with the invention were used in the open air in August-September in a proportion of a spreading dose of 30 m³/ha. The liquid manure used had a solids content of 4 to 8% by weight and contained 4.9% by weight of nitrogen, determined by the Kjeldahl method, 3.9% of phosphorous, calculated as weight of $P_2O_5$ and 2.2% of potassium, calculated as weight of $K_2O$. Each test was completely repeated 3 times and the evaluation of the efficiency was carried out using an evaluation panel consisting of 8 people. The panel was standardized by olfactometry on liquid manure and ammonia. The three components of the efficiency were the following:

| Acceptability | degree of estimation of the residual smell, if it exists, of the treated liquid manure (intolerable, unpleasant, acceptable); |
|---|---|
| Intensity of the smell | degree of perception (imperceptible, detectable to unbearable); |
| Quality of the smell | representativeness of the smell after treatment with respect to the smell of untreated liquid manure (representative smell, unnatural or different). |

The following Tables 2 to 4 show the classification of the formulations according to the percentage of response respectively of:

| their acceptability: | % of "acceptable" responses; |
|---|---|
| their intensity | % of "imperceptible" or "just detectable" responses; |
| their quality | % of "representative of the liquid manure" responses. |

TABLE 2

Classification of the formulations
by their acceptability
(from the best to the worst)

| Formulation No. | % |
|---|---|
| 7b | 100 |
| 4b | 100 |
| 5a | 80 |
| 2b | 78 |
| 6b | 75 |
| 2a | 70 |
| 1a | 68 |
| 7a | 56 |
| 3a | 50 |
| 4a | 30 |
| 6a | 29 |

TABLE 3

Classification of the formulations
by their quality
(from the best to the worst)

| Formulation No. | % |
|---|---|
| 7b | 0 |
| 4b | 0 |
| 5a | 0 |
| 1a | 0 |
| 3a | 0 |
| 2a | 10 |
| 2b | 25 |
| 6b | 25 |
| 6a | 33 |
| 4a | 63 |
| 7a | 67 |

TABLE 4

Classification of the formulations
by their intensity
(from the best to the worst)

| Formulation No. | % |
|---|---|
| 7b | 100 |
| 1a | 67 |
| 5a | 60 |
| 7a | 45 |
| 4b | 33 |
| 2a | 33 |
| 4a | 20 |
| 3a | 17 |
| 6a | 14 |
| 2a | 11 |
| 6b | 0 |

Table 5 shows the combined classification.

TABLE 5

(a) Classification of the formulations 1a to 7a
(b) Combined classification of the formulations

| Formulation No. | Rank | | |
|---|---|---|---|
| | Acceptability | Quality | Intensity |
| (a) | | | |
| 5a | 1 | 1 | 2 |
| 1a | 3 | 1 | 1 |
| 2a | 2 | 2 | 4 |
| 3a | 8 | 1 | 6 |
| 7a | 4 | 5 | 3 |
| 4a | 5 | 4 | 5 |
| 6a | 6 | 3 | 7 |
| (b) | | | |
| 7b | 1 | 1 | 1 |
| 4b | 1 | 1 | 5 |
| 5a | 2 | 1 | 3 |
| 2b | 3 | 3 | 9 |
| 6b | 4 | 3 | 10 |
| 2a | 5 | 2 | 5 |
| 1a | 6 | 1 | 2 |
| 7a | 7 | 6 | 4 |
| 3a | 8 | 1 | 7 |
| 4a | 9 | 5 | 6 |
| 6a | 10 | 4 | 8 |

A person skilled in the art will be able to formulate the deodorizing compositions for animal faeces for each specific application depending on the criteria selected and the costs.

We claim:

1. Composition for deodorizing animal faeces which composition comprises:

(a) at least one normal superphosphate wherein superphosphates consist essentially of mixtures of the three calcium phosphates with phosphoric acid and calcium sulfate; and (b) at least one compound chosen from undecylenic acid, its esters and its polyoxyalkylated esters.

2. Composition according to claim 1, characterized in that the constituent (a) is a normal superphosphate containing approximately 16–18% by weight of $P_2O_5$.

3. Composition according to either of claim 1, characterized in that the constituent (b) is methyl undecylenate.

4. Composition according to one of claim 1, characterized in that it additionally comprises (c) sodium perborate.

5. Deodorizing composition according to one of claims 1 to 4, characterized in that it is formulated in order to be able to treat animal faeces with:

up to approximately 10,000 ppm of the constituent (a);

up to approximately 1000 ppm of the constituent (b); and if appropriate, up to approximately 500 ppm of active $O_2$ from the constituent (c), these amounts being calculated with respect to the weight of the animal faeces to be treated.

6. Deodorizing composition according to claim 5, characterized in that it is formulated in order to be able to treat animal faeces with:

approximately 1000 to 5000 ppm of the constituent (a);

approximately 50 to 100 ppm of the constituent (b); and if appropriate, up to approximately 300 ppm of active $O_2$ from the constituent (c), these amounts being calculated with respect to the weight of the animal faeces to be treated.

7. Deodorizing composition according to claim 6, characterized in that it is formulated in order to be able to treat animal faeces with:

approximately 1000 to 5000 ppm of the constituent (a); and approximately 50 to 100 ppm of the constituent (b);

and further characterized in that the constituent (c) is present in an amount which makes it possible to treat the animal faeces with approximately 150 to 300 ppm of active $O_2$.

8. Deodorizing composition according to claim 1, characterized in that it additionally comprises at least one additive chosen from fungicides and bacteriostatic agents.

9. Deodorizing composition according to claim 1, characterized in that its constituents are packaged separately before use.

10. Deodorizing composition according to claim 1, characterized in that each of its constituents is provided in a pulverulent form, or else in suspension or in solution in water, or else at least partially in the form adsorbed on a porous and inert carrier such as silica or clay particles.

11. Process for deodorizing liquid manure, in particular liquid pig manure, characterized in that a composition as defined in claim 1 is incorporated, by mixing, in the animal faeces to be treated, with a view to storing or spreading them.

12. Process according to claim 11, characterized in that the mixture of the constituents of the composition is prepared only at the time of use.

13. Process according to claim 11, characterized in that, at the time of use, at least one constituent of the composition is incorporated, separately from the other constituents, in the animal faeces to be treated.

14. The composition according to claim 1 for deodorizing liquid manure.

15. The composition according to claim 14 for deodorizing liquid pig manure.

* * * * *